US010226231B2

(12) United States Patent
Nishihara et al.

(10) Patent No.: US 10,226,231 B2
(45) Date of Patent: Mar. 12, 2019

(54) ULTRASONIC DIAGNOSTIC APPARATUS AND IMAGE PROCESSING APPARATUS

(71) Applicant: Toshiba Medical Systems Corporation, Otawara-shi (JP)

(72) Inventors: Kuramitsu Nishihara, Otawara (JP); Muneki Kataguchi, Nasushiobara (JP); Akihiro Kakee, Nasushiobara (JP); Mio Azegami, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 121 days.

(21) Appl. No.: 14/088,086

(22) Filed: Nov. 22, 2013

(65) Prior Publication Data

US 2014/0081141 A1  Mar. 20, 2014

Related U.S. Application Data

(63) Continuation of application No. PCT/JP2012/061899, filed on May 9, 2012.

(30) Foreign Application Priority Data

May 24, 2011  (JP) .............................. 2011-115935

(51) Int. Cl.
  *A61B 8/00* (2006.01)
  *A61B 8/08* (2006.01)
  (Continued)

(52) U.S. Cl.
  CPC ............ *A61B 8/463* (2013.01); *A61B 8/0883* (2013.01); *A61B 8/462* (2013.01); *A61B 8/466* (2013.01);
  (Continued)

(58) Field of Classification Search
  None
  See application file for complete search history.

(56) References Cited

U.S. PATENT DOCUMENTS 4,925,294 A * 5/1990 Geshwind ............ H04N 19/597
                                                   348/E13.008
5,993,391 A * 11/1999 Kamiyama .............. A61B 8/10
                                                   128/916
(Continued)

FOREIGN PATENT DOCUMENTS

CN  101322155 A  12/2008
JP  06-319737 A  11/1994
(Continued)

OTHER PUBLICATIONS

Prema, Vijay, Gary Roberts, and B. C. Wuensche. "3D visualisation techniques for multi-layer display technology." IVCNZ. vol. 6. 2006.*
(Continued)

*Primary Examiner* — Carolyn Pehlke
(74) *Attorney, Agent, or Firm* — Oblon, McClelland, Maier & Neustadt, L.L.P.

(57) ABSTRACT

In an ultrasonic diagnostic apparatus according to an embodiment, a separator separates an arbitrary region of a displayed object represented from image data, in a depth direction, based on a characterizing quantity included in the image data. An image generation controller generates an image to be displayed in which depth direction information is reflected on the arbitrary region of the displayed object, separated by the separator. A display controller causes a monitor being capable of providing a stereoscopic vision to display the image to be displayed generated by the image generation controller.

10 Claims, 9 Drawing Sheets

(51) Int. Cl.
*G06T 7/00* (2017.01)
*H04N 13/00* (2018.01)
*H04N 13/04* (2006.01)

(52) U.S. Cl.
CPC .............. *A61B 8/483* (2013.01); *A61B 8/488* (2013.01); *A61B 8/5207* (2013.01); *A61B 8/54* (2013.01); *G06T 7/0012* (2013.01); *H04N 13/0022* (2013.01); *H04N 13/0404* (2013.01); *H04N 13/0438* (2013.01)

(56) References Cited

U.S. PATENT DOCUMENTS

| | | | |
|---|---|---|---|
| 6,116,244 A * | 9/2000 | Hossack et al. | 600/441 |
| 6,638,228 B1 * | 10/2003 | Brock-Fisher et al. | 600/443 |
| 2006/0173338 A1 * | 8/2006 | Ma et al. | 600/456 |
| 2007/0255138 A1 * | 11/2007 | Kristofferson et al. | 600/443 |
| 2008/0303894 A1 | 12/2008 | Ernst et al. | |

FOREIGN PATENT DOCUMENTS

| | | |
|---|---|---|
| JP | 2005-278988 A | 10/2005 |
| JP | 2008-000181 A | 1/2008 |
| JP | 2009-517951 A | 4/2009 |
| JP | 2009-520231 A | 5/2009 |
| JP | 2010-113332 A | 5/2010 |

OTHER PUBLICATIONS

International Search Report dated Jun. 12, 2012 for PCT/JP2012/061899 filed on May 9, 2012 with English Translation.
International Written Opinion dated Jun. 12, 2012 for PCT/JP2012/061899 filed on May 9, 2012.
Combined Office Action and Search Report dated Dec. 23, 2014 in Chinese Patent Application No. 201280024418.5 (with English translation of categories of cited documents).
Office Action dated May 26, 2015 in Japanese Patent Application No. 2011-115935.

* cited by examiner

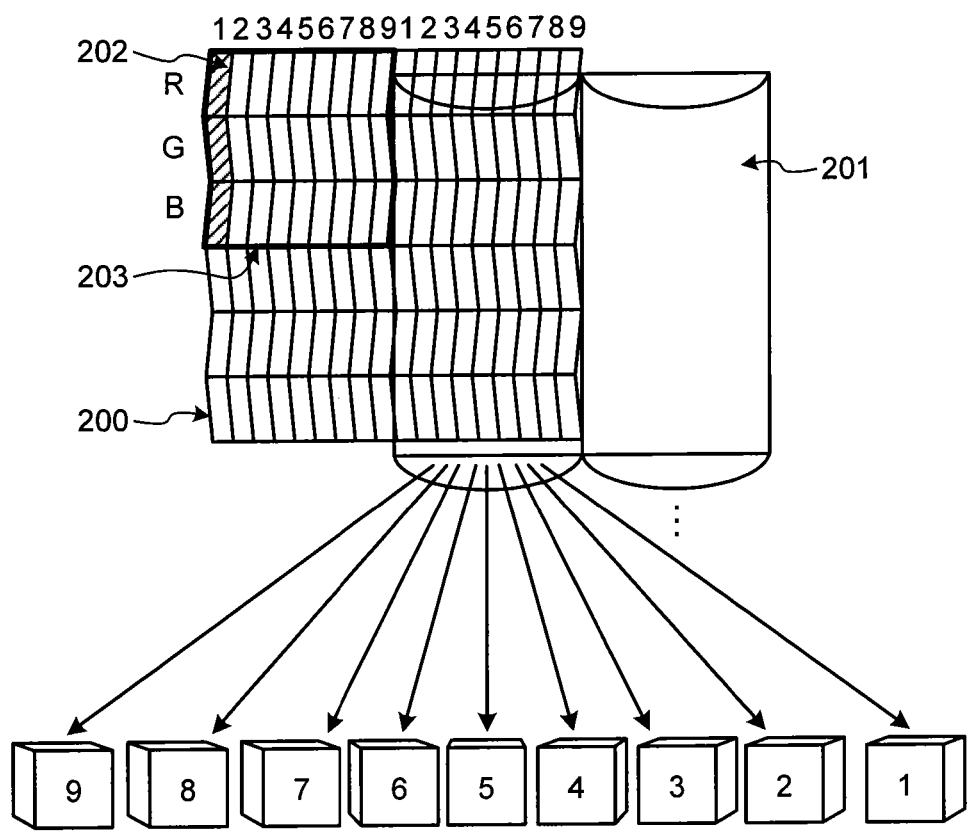

FIG. 8
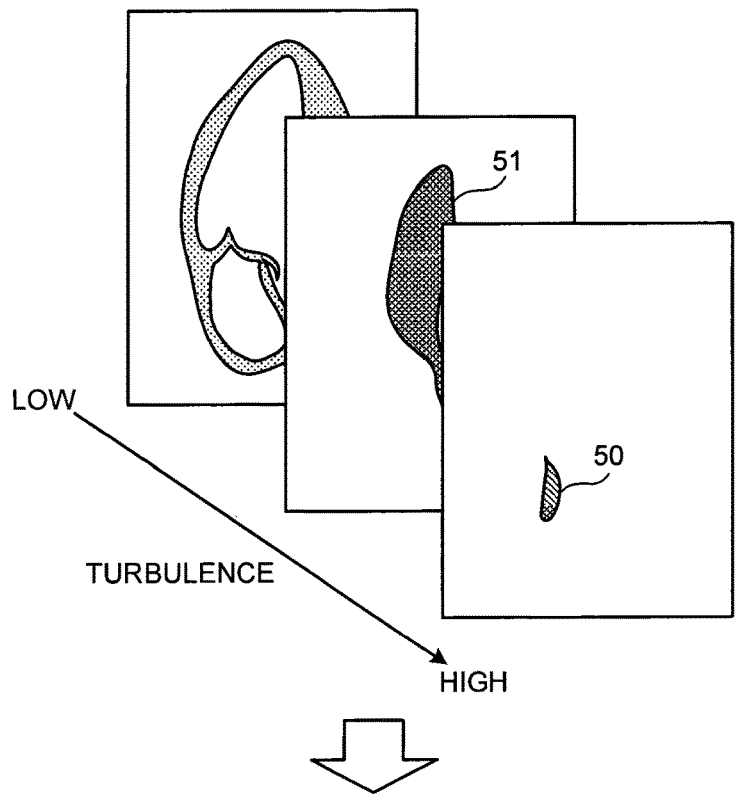
(A)
LOW
TURBULENCE
HIGH
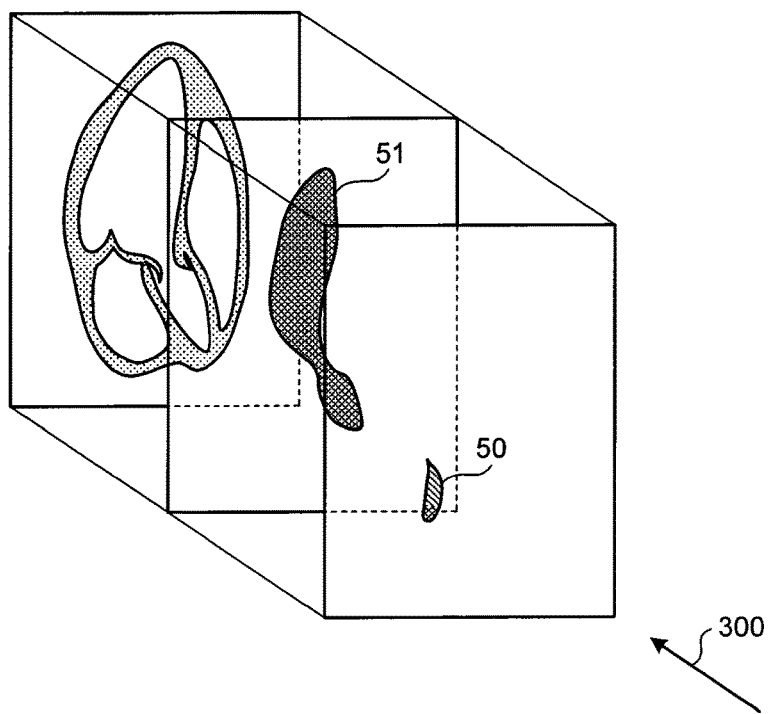
(B) VIRTUAL VOLUME DATA
300

FIG.9
(A)
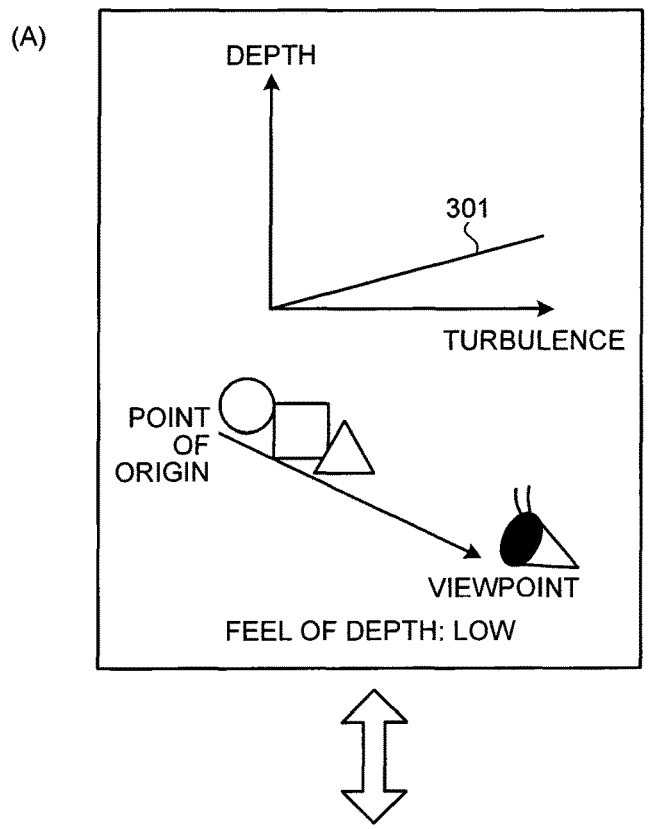
(B)
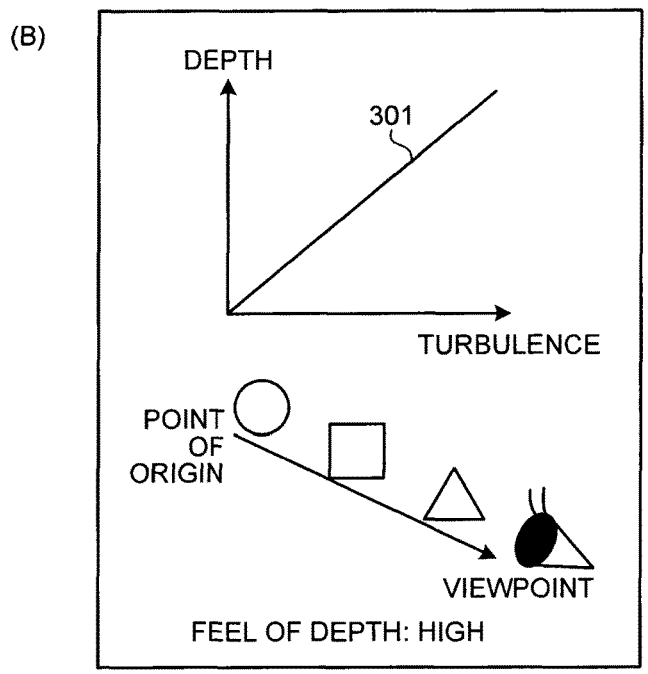

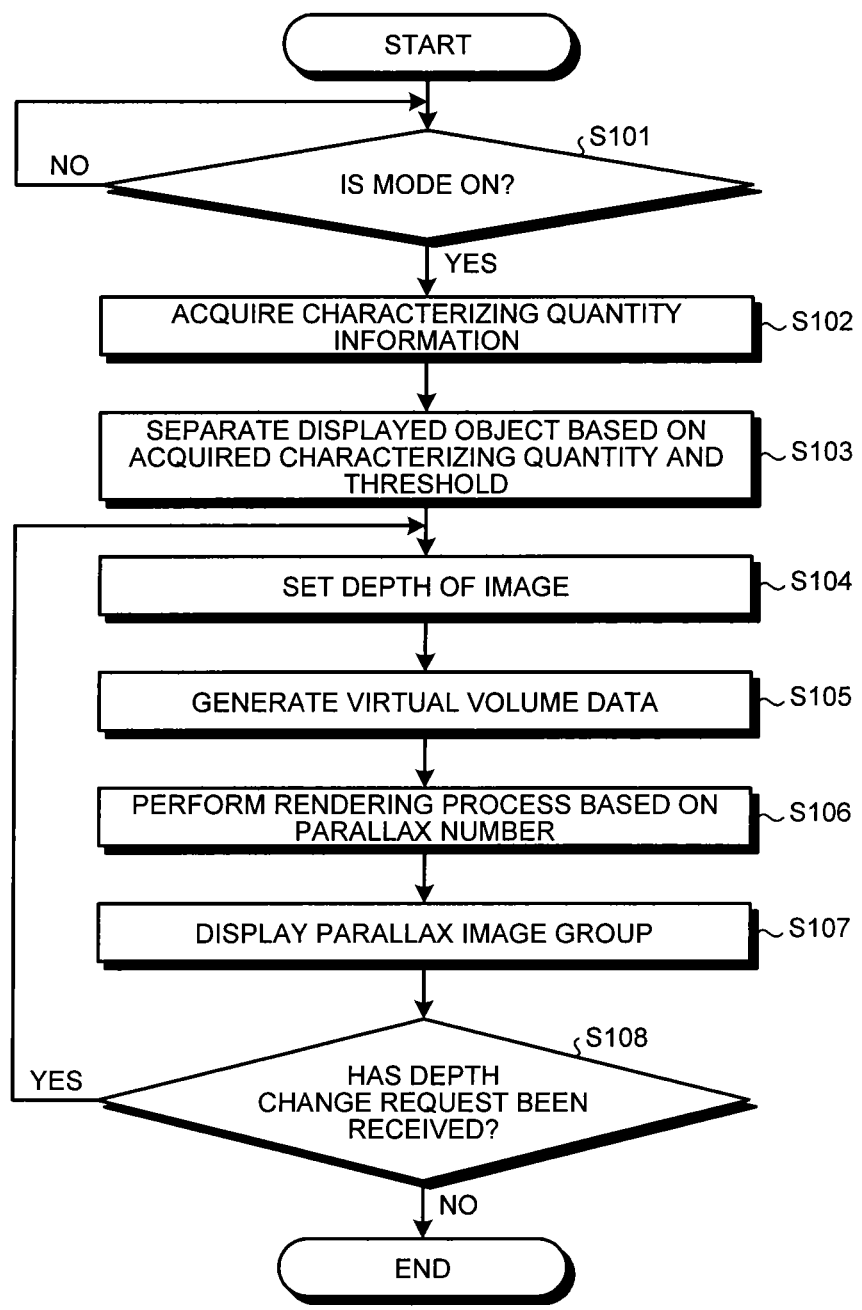

US 10,226,231 B2

ULTRASONIC DIAGNOSTIC APPARATUS AND IMAGE PROCESSING APPARATUS

CROSS-REFERENCE TO RELATED APPLICATION(S)

This application is a continuation of International Application No. PCT/JP2012/061899, filed on May 9, 2012 which claims the benefit of priority of the prior Japanese Patent Application No. 2011-115935, filed on May 24, 2011, the entire contents of which are incorporated herein by reference.

FIELD

Embodiments described herein relate generally to an ultrasonic diagnostic apparatus and an image processing apparatus.

BACKGROUND

Ultrasonic diagnostic apparatuses have been conventionally used in medical care today in examining or diagnosing various types of body tissues such as those of a heart, a liver, a kidney, and a mammary gland. Ultrasonic diagnostic apparatuses has advantages over other medical image diagnostic apparatuses, such as X-ray diagnostic apparatuses and X-ray computed tomographic imaging apparatuses, in that they are easier to use and non-intrusive to subjects without the risk of radiation exposure, for example.

Such an ultrasonic diagnostic apparatus generates and displays a tomographic image (B-mode image) of a tissue structure in a subject by transmitting ultrasound waves from an ultrasound probe, and receiving reflection wave signals reflected on the internal tissues of the subject. A more recent ultrasonic diagnostic apparatus generates and displays a color Doppler image presenting blood flow information such as the velocity, turbulence, and power of blood flows in a distinguishable manner by colors, by taking advantage of the Doppler shift of ultrasonic waves, as well as a region where the blood flows are present within a subject. There have been situations where visibility of an image captured by such an ultrasonic diagnostic apparatus is degraded.

BRIEF DESCRIPTION OF THE DRAWINGS

FIG. 3 is a schematic for explaining an example of a stereoscopic display monitor providing a stereoscopic vision using nine-parallax images;

FIG. 8 is a schematic for explaining an example performed by an image generation controller in the first embodiment;

FIG. 9 is a schematic for explaining an example of a process performed by a depth setting module in the first embodiment; and FIG. 10 is a flowchart illustrating a process performed by the ultrasonic diagnostic apparatus in the first embodiment.

DETAILED DESCRIPTION

According to an embodiment, an ultrasonic diagnostic apparatus includes a separator, an image generator and a display controller. The separator configured to separate an arbitrary region of a displayed object represented from image data, in a depth direction, based on a characterizing quantity included in the image data. The image generator configured to generate an image to be displayed in which information of the depth direction is reflected on the arbitrary region of the displayed object, the region being separated by the separator. The display controller configured to cause a display unit being capable of providing a stereoscopic vision to display the image to be displayed generated by the image generator.

An ultrasonic diagnostic apparatus and an image processing apparatus according to an embodiment will be explained in detail with reference to the accompanying drawings. To begin with, terms used in the embodiment below will be explained. A "parallax image group" is a group of images generated by applying a volume rendering process to volume data while shifting viewpoint positions by a given parallax angle. In other words, a "parallax image group" includes a plurality of "parallax images" each of which has a different "viewpoint position". A "parallax angle" is an angle determined by adjacent viewpoint positions among viewpoint positions specified for generation of the "parallax image group" and a given position in a space represented by the volume data (e.g., the center of the space). A "parallax number" is the number of "parallax images" required for a stereoscopic vision on a stereoscopic display monitor. A "nine-parallax image" mentioned below means a "parallax image group" with nine "parallax images". A "two-parallax image" mentioned below means a "parallax image group" with two "parallax images". A "stereoscopic image" mentioned below is a three-dimensional image observed by an observer when a parallax image group is output and displayed by a display unit being capable of providing a stereoscopic vision.

First Embodiment

Figure 1:
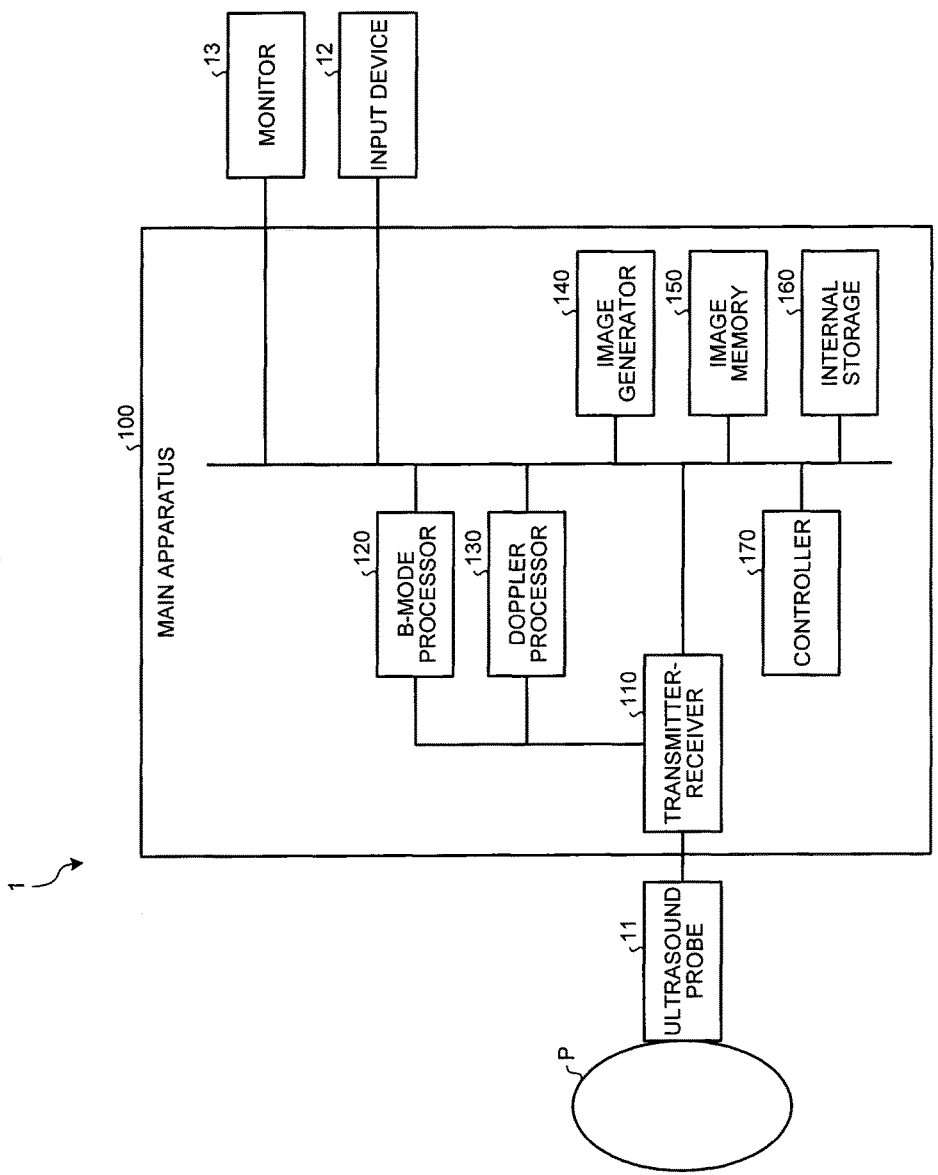
FIG. 1 is a schematic of an example of an overall structure of an ultrasonic diagnostic apparatus according to a first embodiment.

An overall structure of an ultrasonic diagnostic apparatus according to a first embodiment will be explained with reference to FIG. 1. FIG. 1 is a schematic of an example of an overall structure of an ultrasonic diagnostic apparatus 1 according to the first embodiment. As illustrated in FIG. 1, the ultrasonic diagnostic apparatus 1 according to the first embodiment includes an ultrasound probe 11, an input device 12, a monitor 13, and a main apparatus 100.

The ultrasound probe 11 includes a plurality of piezoelectric vibrators. The piezoelectric vibrators generate ultrasonic waves based on driving signals supplied by a transmitter-receiver 110 provided in the main apparatus 100, which is to be explained later, and receives reflection waves from a subject P and converts the reflection waves into electrical signals. The ultrasound probe 11 also includes matching layers provided on the piezoelectric vibrators, and a backing material for preventing the ultrasonic waves from propagating backwardly from the piezoelectric vibrators.

When an ultrasonic wave is transmitted from the ultrasound probe 11 toward the subject P, the ultrasonic wave thus transmitted is reflected one after another on a discontinuous acoustic impedance surface in body tissues within the subject P, and received as reflection wave signals by the piezoelectric vibrators in the ultrasound probe 11. The amplitude of the reflection wave signals thus received depends on an acoustic impedance difference on the discontinuous surface on which the ultrasonic wave is reflected. When a transmitted ultrasonic wave pulse is reflected on the surface of a moving blood flow or of a cardiac wall, the frequency of the reflection wave signal thus received is shifted by the Doppler shift depending on the velocity component of the moving body with respect to the direction in which the ultrasonic wave is transmitted.

The embodiment is applicable to both cases where the subject P is scanned two-dimensionally using an ultrasound probe 11 being a one-dimensional ultrasound probe in which a plurality of piezoelectric vibrators are arranged in a line, and where the subject P is scanned three-dimensionally using an ultrasound probe 11 in which a plurality of piezoelectric vibrators included in a one-dimensional ultrasound probe are mechanically swung or using an ultrasound probe 11 being a two-dimensional ultrasound probe having a plurality of piezoelectric vibrators arranged two-dimensionally in a grid.

The input device 12 includes a mouse, a keyboard, a button, a panel switch, a touch command screen, a foot switch, and a track ball, for example. The input device 12 receives various setting requests from an operator of the ultrasonic diagnostic apparatus 1, and forwards the various setting requests thus received to the main apparatus 100. For example, the input device 12 receives an input operation for setting the depth of a stereoscopic image.

The monitor 13 displays a graphical user interface (GUI) for allowing the operator of the ultrasonic diagnostic apparatus 1 to input various setting requests using the input device 12, and an ultrasound image generated by the main apparatus 100, for example.

The monitor 13 is a monitor enabled for a stereoscopic vision (hereinafter, referred to as a stereoscopic display monitor), and displays various types of information. For example, the monitor 13 displays a parallax image group generated by the main apparatus 100, and a GUI for receiving various instructions from an operator.

The stereoscopic display monitor will now be explained. A common, general-purpose monitor that is most widely used today displays two-dimensional images two-dimensionally, and is not capable of displaying a two-dimensional image stereoscopically. If an observer wishes for a stereoscopic vision on the general-purpose monitor, an apparatus outputting images to the general-purpose monitor needs to display two-parallax images in parallel that can be perceived by the observer stereoscopically, using a parallel technique or a crossed-eye technique. Alternatively, the apparatus outputting images to the general-purpose monitor needs to present images that can be perceived stereoscopically by the observer using anaglyph, which uses a pair of glasses having a red filter for the left eye and a blue filter for the right eye, for example.

Furthermore, some stereoscopic display monitors enable two-parallax images (also referred to as binocular parallax images) to be perceived stereoscopically using special equipment such as a pair of stereoscopic glasses.

Figure 2A:
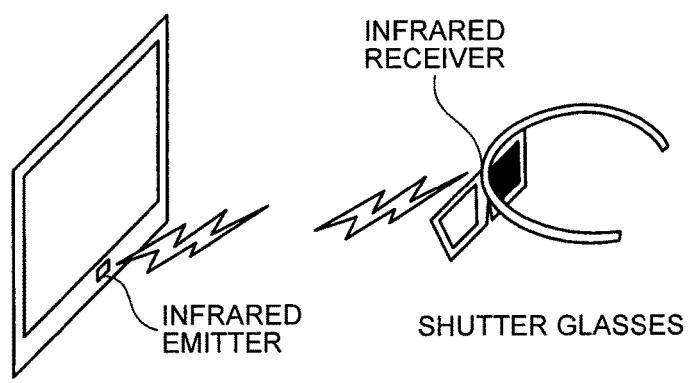
FIG. 2A is a schematic for explaining an example of a stereoscopic display monitor providing a stereoscopic vision using two-parallax images.
Figure 2B:
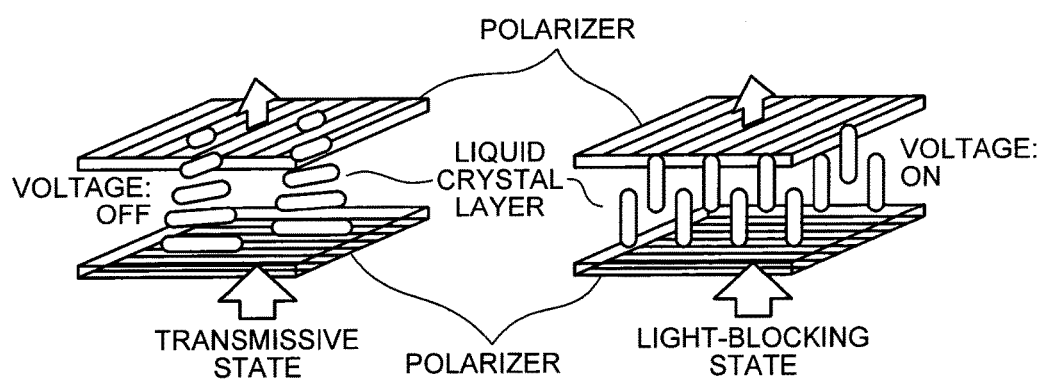
FIG. 2B is a schematic for explaining an example of a stereoscopic display monitor providing a stereoscopic vision using two-parallax images.

FIGS. 2A and 2B are schematics for explaining an example of a stereoscopic display monitor providing a stereoscopic vision using two-parallax images. The example illustrated in FIGS. 2A and 2B represents a stereoscopic display monitor providing a stereoscopic vision using a shutter technique. In this example, a pair of shutter glasses are used as stereoscopic glasses worn by an observer who observes the monitor. The stereoscopic display monitor outputs two-parallax images onto the monitor alternatingly. For example, the monitor illustrated in FIG. 2A outputs an image for the left eye and an image for the right eye alternatingly at 120 hertz. An infrared emitter is installed in the monitor, as illustrated in FIG. 2A, and the infrared emitter controls infrared outputs based on the timing at which the images are swapped.

The infrared output from the infrared emitter is received by an infrared receiver provided on the shutter glasses illustrated in FIG. 2A. A shutter is installed on the frame on each side of the shutter glasses. The shutter glasses switch the right shutter and the left shutter between a transmissive state and a light-blocking state alternatingly based on the timing at which the infrared receiver receives infrared. A process of switching the shutters between the transmissive state and the light-blocking state will now be explained.

As illustrated in FIG. 2B, each of the shutters includes an incoming polarizer and an outgoing polarizer, and also includes a liquid crystal layer interposed between the incoming polarizer and the outgoing polarizer. The incoming polarizer and the outgoing polarizer are orthogonal to each other, as illustrated in FIG. 2B. In an "OFF" state during which a voltage is not applied as illustrated in FIG. 2B, the light having passed through the incoming polarizer is rotated by 90 degrees by the effect of the liquid crystal layer, and thus passes through the outgoing polarizer. In other words, a shutter with no voltage applied is in the transmissive state.

By contrast, as illustrated in FIG. 2B, in an "ON" state during which a voltage is applied, the polarization rotation effect of liquid crystal molecules in the liquid crystal layer is lost. Therefore, the light having passed through the incoming polarizer is blocked by the outgoing polarizer. In other words, the shutter applied with a voltage is in the light-blocking state.

The infrared emitter outputs infrared for a time period while which an image for the left eye is displayed on the monitor, for example. During the time the infrared receiver is receiving infrared, no voltage is applied to the shutter for the left eye, while a voltage is applied to the shutter for the right eye. In this manner, as illustrated in FIG. 2A, the shutter for the right eye is in the light-blocking state and the shutter for the left eye is in the transmissive state to cause the image for the left eye to enter the left eye of the observer. For a time period while which an image for the right eye is displayed on the monitor, the infrared emitter stops outputting infrared. When the infrared receiver receives no infrared, a voltage is applied to the shutter for the left eye, while no voltage is applied to the shutter for the right eye. In this manner, the shutter for the left eye is in the light-blocking state, and the shutter for the right eye is in the transmissive state to cause the image for the right eye to enter the right eye of the observer. As explained above, the stereoscopic display monitor illustrated in FIGS. 2A and 2B makes a display that can be stereoscopically perceived by the observer, by switching the states of the shutters in association with the images displayed on the monitor. Also known as a stereoscopic display monitor being capable of displaying two-parallax images stereoscopically is a monitor for which a pair of polarized glasses are used, in addition to the shutter technique explained above.

Some stereoscopic display monitors that have recently been put into practical use allow multiple-parallax images, e.g., nine-parallax images, to be stereoscopically viewed by an observer with the naked eyes, by adopting a light ray controller such as a lenticular lens. Such a stereoscopic display monitor enables stereoscopy using the binocular parallax, and also enables stereoscopy using moving parallax, where a video observed by an observer changes following the movement of the observer's viewpoint.

FIG. 3 is a schematic for explaining an example of a stereoscopic display monitor providing a stereoscopic vision using nine-parallax images. In the stereoscopic display monitor illustrated in FIG. 3, a light ray controller is arranged on the front surface of a flat display screen 200 such as a liquid crystal panel. For example, in the stereoscopic display monitor illustrated in FIG. 3, a vertical lenticular sheet 201 having an optical aperture extending in a vertical direction is fitted on the front surface of the display screen 200 as a light ray controller. Although the vertical lenticular sheet 201 is fitted so that the convex of the vertical lenticular sheet 201 faces the front side in the example illustrated in FIG. 3, the vertical lenticular sheet 201 may be also fitted so that the convex faces the display screen 200.

As illustrated in FIG. 3, the display screen 200 has pixels 202 that are arranged in a matrix. Each of the pixels 202 has an aspect ratio of 3:1, and includes three sub-pixels of red (R), green (G), and blue (B) that are arranged vertically. The stereoscopic display monitor illustrated in FIG. 3 converts nine-parallax images consisting of nine images into an intermediate image in a given format (e.g., a grid-like format), and outputs the result onto the display screen 200. In other words, the stereoscopic display monitor illustrated in FIG. 3 assigns and outputs nine pixels located at the same position in the nine-parallax images to the pixels 202 arranged in nine columns. The pixels 202 arranged in nine columns function as a unit pixel group 203 that displays nine images from different viewpoint positions at the same time.

The nine-parallax images simultaneously output as the unit pixel group 203 onto the display screen 200 are emitted with a light emitting diode (LED) backlight, for example, as parallel rays, and travel further in multiple directions through the vertical lenticular sheet 201. Light for each of the pixels included in the nine-parallax images is output in multiple directions, whereby the light entering the right eye and the left eye of the observer changes as the position (viewpoint position) of the observer changes. In other words, depending on the angle from which the observer perceives, the parallax image entering the right eye and the parallax image entering the left eye are at different parallax angles. Therefore, the observer can perceive a captured object stereoscopically from any one of the nine positions illustrated in FIG. 3, for example. At the position "5" illustrated in FIG. 3, the observer can perceive the captured object stereoscopically as the object faces directly the observer. At each of the positions other than the position "5" illustrated in FIG. 3, the observer can perceive the captured object stereoscopically with its orientation changed. The stereoscopic display monitor illustrated in FIG. 3 is merely an example. The stereoscopic display monitor for displaying nine-parallax images may be a liquid crystal display with horizontal stripes of "RRR . . . , GGG . . . , BBB . . . " as illustrated in FIG. 3, or a liquid crystal display with vertical stripes of "RGBRGB . . . ". The stereoscopic display monitor illustrated in FIG. 3 may be a monitor using a vertical lens in which the lenticular sheet is arranged vertically as illustrated in FIG. 3, or a monitor using a diagonal lens in which the lenticular sheet is arranged diagonally.

Referring back to FIG. 1, the main apparatus 100 is an apparatus for generating an ultrasound image based on the reflection waves received by the ultrasound probe 11, and includes the transmitter-receiver 110, a B-mode processor 120, a Doppler processor 130, an image generator 140, an image memory 150, an internal storage 160, and a controller 170, as illustrated in FIG. 1.

The transmitter-receiver 110 includes a trigger generator circuit, a delay circuit, a pulsar circuit, and the like, and supplies a driving signal to the ultrasound probe 11. The pulsar circuit generates a rate pulse for generating ultrasonic waves to be transmitted, repeatedly at a given rate frequency. The delay circuit adds a delay time corresponding to each of the piezoelectric vibrators to each of the rate pulses generated by the pulsar circuit. Such a delay time is required for determining the transmission directivity by converging the ultrasonic waves generated in the ultrasound probe 11 into a beam. The trigger generator circuit applies the driving signal (driving pulse) to the ultrasound probe 11 at a timing based on the rate pulse. In other words, by causing the delay circuit to change the delay time to be added to each of the rate pulses, the direction in which the ultrasonic waves are transmitted from each piezoelectric vibrator surface is adjusted to a given direction.

The transmitter-receiver 110 also includes an amplifier circuit, an analog-to-digital (A/D) converter, and an adder, and generates reflection wave data by applying various processes to the reflection wave signal received by the ultrasound probe 11. The amplifier circuit amplifies the reflection wave signal on each channel, and performs a gain correction. The A/D converter performs an A/D conversion on the reflection wave signal having gain corrected, and adds a delay time required for determining a reception directivity. The adder performs an addition on the reflection wave signal processed by the A/D converter, and generates the reflection wave data. Through the addition performed by the adder, a reflection component in the direction corresponding to the reception directivity of the reflection wave signal is emphasized.

In the manner described above, the transmitter-receiver 110 controls the transmission directivity and the reception directivity of the ultrasonic wave transmissions and receptions. The transmitter-receiver 110 has a function for enabling delay information, a transmission frequency, a transmit driving voltage, and a numerical aperture, for example, to be changed instantaneously under control performed by the controller 170 to be described later. In particular, a change in the transmission driving voltage is performed by a linearly amplifying oscillation circuit that is cable of switching values instantaneously, or a mechanism for electrically switching a plurality of power units. The transmitter-receiver 110 is also capable of transmitting and receiving a different waveform for every frame or every rate.

The B-mode processor 120 receives the reflection wave data that is a processed reflection wave signal applied with the gain correction, the A/D conversion, and the addition by the transmitter-receiver 110, and performs a logarithmic amplification, an envelope detection, and the like, to generate data in which signal intensity is represented as a brightness level (B-mode data).

The B-mode processor 120 can change the bandwidth of frequencies to be visualized by changing a detecting frequency. The B-mode processor 120 is capable of performing parallel detections on a single piece of received data, using two detecting frequencies.

From a single piece of data received from a region of interest in the subject P to which an ultrasound contrast agent is injected, reflection wave data resulted from the ultrasound contrast agent (microbubbles, bubbles) flowing through the region of interest can be separated from reflection wave data resulted from the tissues in the region of interest, by using the function of the B-mode processor 120, and the image generator 140 to be described later can generate a contrast image in which the flowing bubbles are visualized highly sensitively, and a histological image in which tissues are visualized in a manner allowing their forms to be observed.

The Doppler processor 130 frequency-analyzes velocity information in the reflection wave data received from the transmitter-receiver 110, and extracts blood flows, tissues, and contrast agent echo components resulted from the Doppler shift, and generates data (Doppler data) that is moving body information such as average velocity, turbulence, power, and the like extracted for a plurality of points.

More specifically, the Doppler processor 130 is a processor being cable of performing tissue Doppler imaging (TDI) and color Doppler imaging (CDI). In other words, the Doppler processor 130 is a processor that acquires movement information of tissues in a scanned area (tissue movement information), and generates tissue Doppler data that is used for generating a tissue Doppler image, which indicates behaviors of the tissues. The Doppler processor 130 is also a processor that acquires movement information of blood flows existing in a scanned area (blood flow movement information), and generates color Doppler data that is used for generating a color Doppler image, which indicates behaviors of the blood flows.

The B-mode processor 120 and the Doppler processor 130 according to the first embodiment are capable of processing both two-dimensional reflection wave data and three-dimensional reflection wave data. In other words, the B-mode processor 120 according to the first embodiment is capable of generating three-dimensional B-mode data from three-dimensional reflection wave data. The Doppler processor 130 according to the first embodiment is capable of generating three-dimensional Doppler data from three-dimensional reflection wave data.

The image generator 140 generates ultrasound images from the data generated by the B-mode processor 120 and the Doppler processor 130. In other words, the image generator 140 generates a B-mode image in which the intensity of a reflection wave is represented as a luminance from the B-mode data generated by the B-mode processor 120. The image generator 140 is also capable of generating a three-dimensional B-mode image from the three-dimensional B-mode data generated by the B-mode processor 120.

The image generator 140 generates an average velocity image, a turbulence image, or a power image representing the moving body information or a color Doppler image being a combination of these images, from the Doppler data generated by the Doppler processor 130. The image generator 140 is also cable of generating a three-dimensional color Doppler image from the three-dimensional Doppler data generated by the Doppler processor 130.

Generally, the image generator 140 converts rows of scan line signals from an ultrasound scan into rows of scan line signals in a video format, typically one used for television (performs a scan conversion), to generate an ultrasound image being an image to be displayed. Specifically, the image generator 140 generates an ultrasound image as an image to be displayed by performing a coordinate conversion in accordance with the way ultrasound scan is performed with the ultrasound probe 11. In addition to the scan conversion, the image generator 140 performs various image processes using, for example, a plurality of image frames applied with the scan conversion, such as an image process for re-generating an image with averaged luminance (smoothing process) and an image process performed in the image with a differential filter (edge enhancement process).

The image generator 140 is capable of generating various images for displaying the volume data onto the monitor 13. Specifically, the image generator 140 is capable of generating a multi-planar reconstruction (MPR) image or a rendering image (volume rendering image or surface rendering image) from the volume data. Volume data herein includes a three-dimensional B-mode image, a three-dimensional color Doppler image, or virtual volume data plotted in a virtual three-dimensional space.

Figure 4:
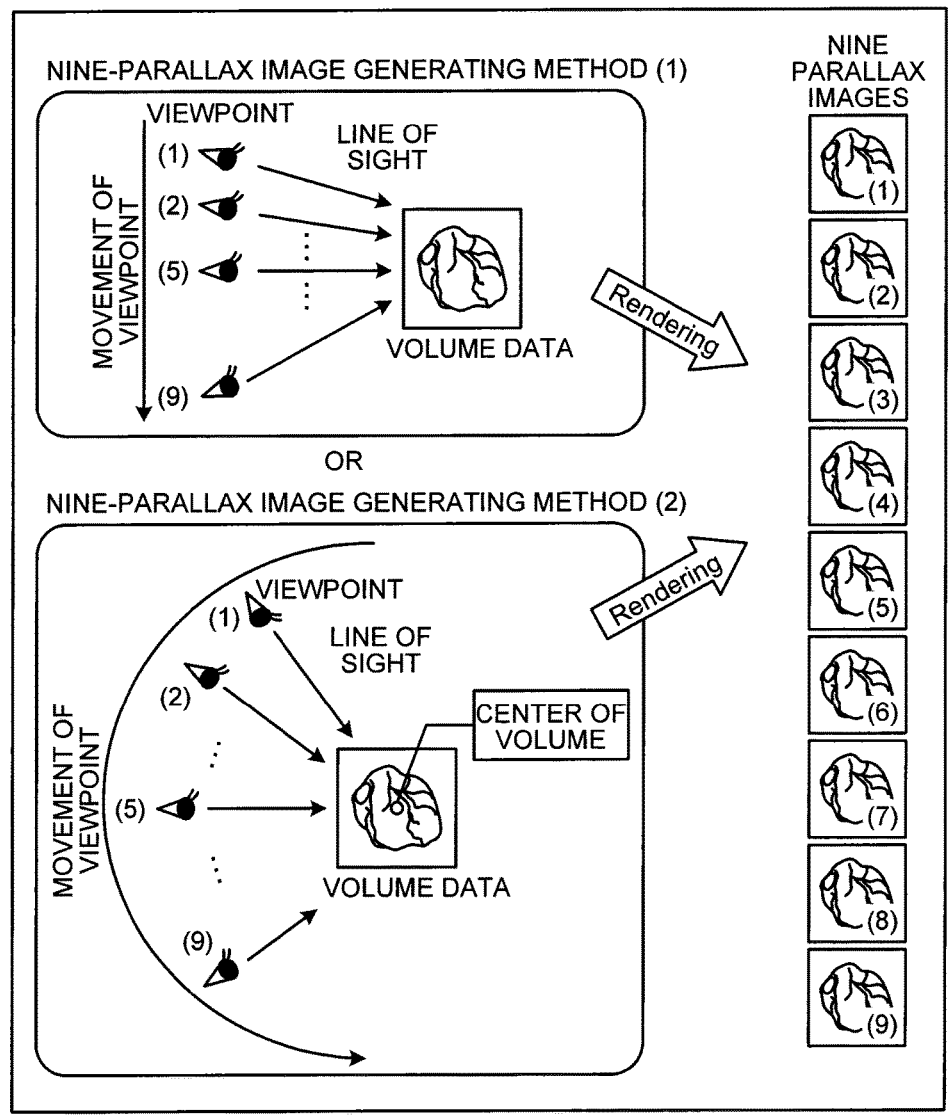
FIG. 4 is a schematic for explaining an example of a volume rendering process performed by an image generator in the first embodiment.

An example of a process of generating a volume rendering image performed by the image generator 140 will now be explained. FIG. 4 is a schematic for explaining an example of the volume rendering process performed by the image generator 140 according to the first embodiment. For example, it is assumed herein that the image generator 140 receives parallel projection as a rendering condition, and a reference viewpoint position (5) and a parallax angle of "one degree", as illustrated in the "nine-parallax image generating method (1)" in FIG. 4. In such a case, the image generator 140 generates nine parallax images, each having a parallax angle (angle between the lines of sight) shifted by one degree, by parallel projection, by moving the position of the viewpoint from (1) to (9) in such a way that the parallax angles are set in every "one degree". Before performing the parallel projection, the image generator 140 establishes a light source radiating parallel light rays from the infinity along the line of sight.

It is assumed now that the image generator 140 receives perspective projection as a rendering condition, and a reference viewpoint position (5) and a parallax angle of "one degree", as illustrated in the "nine-parallax image generating method (2)" in FIG. 4. In such a case, the image generator 140 generates nine parallax images, each having a parallax angle shifted by one degree, by perspective projection, by moving the position of the viewpoint from (1) to (9) around the center (the center of gravity) of the volume data in such a way that the parallax angle is set in every "one degree". Before performing the perspective projection, the image generator 140 establishes a point light source or a surface light source radiating light three-dimensionally about the line of sight, for each of the viewpoints. Alternatively, when the perspective projection is to be performed, the viewpoints (1) to (9) may be shifted in parallel depending on rendering conditions. The line of sight is laid in a direction extending from the viewpoint to the center (the center of gravity) of a cross-sectional surface of the volume data, as illustrated in FIG. 4.

The image generator 140 may also perform a volume rendering process using both parallel projection and perspective projection, by establishing a light source radiating light two-dimensionally, radially from a center on the line of sight for the vertical direction of the volume rendering image to be displayed, and radiating parallel light rays from the infinity along the line of sight for the horizontal direction of the volume rendering image to be displayed.

The parallax image group generated by the image generator 140 is stored in the image memory 150. The ultrasonic diagnostic apparatus 1 then converts the parallax image group into an intermediate image in which the parallax image group is arranged in a predetermined format (e.g., a grid-like format), for example, and displays the image onto the stereoscopic display monitor. In this manner, the stereoscopic image can be presented to physicians and ultrasonographers who are users.

Referring back to FIG. 1, the image memory 150 stores therein raw data (B-mode data and Doppler data) generated by the B-mode processor 120 and the Doppler processor 130 and an ultrasound image to be displayed generated by the image generator 140, and virtual volume data generated under the control of the controller 170, which is to be described later. The virtual volume data will be explained later in detail. The image memory 150 also stores therein output signal (radio frequency (RF)) immediately after being processed by the transmitter-receiver 110, a luminance signal of an image, and various raw data as necessary.

The internal storage 160 stores therein control programs for transmitting and receiving ultrasonic waves, performing the image processes and a displaying process, and various data such as diagnostic information (e.g., a patient identification (ID) and observations by a physician), and diagnostic protocols. The internal storage 160 is also used to store therein the image stored in the image memory 150 as required.

The controller 170 controls the overall process performed in the ultrasonic diagnostic apparatus 1. Specifically, the controller 170 controls the processes performed by the transmitter-receiver 110, the B-mode processor 120, the Doppler processor 130, and the image generator 140, and controls to display an ultrasound image stored in the image memory 150 onto the monitor 13 based on various setting requests input by the operator via the input device 12, or various control programs and various setting information read from the internal storage 160.

The overall configuration of the ultrasonic diagnostic apparatus 1 according to the first embodiment is as explained above. The ultrasonic diagnostic apparatus 1 according to the first embodiment having such a configuration is configured to improve image visibility under the control performed by the controller 170 to be explained below in detail.

Figure 5:
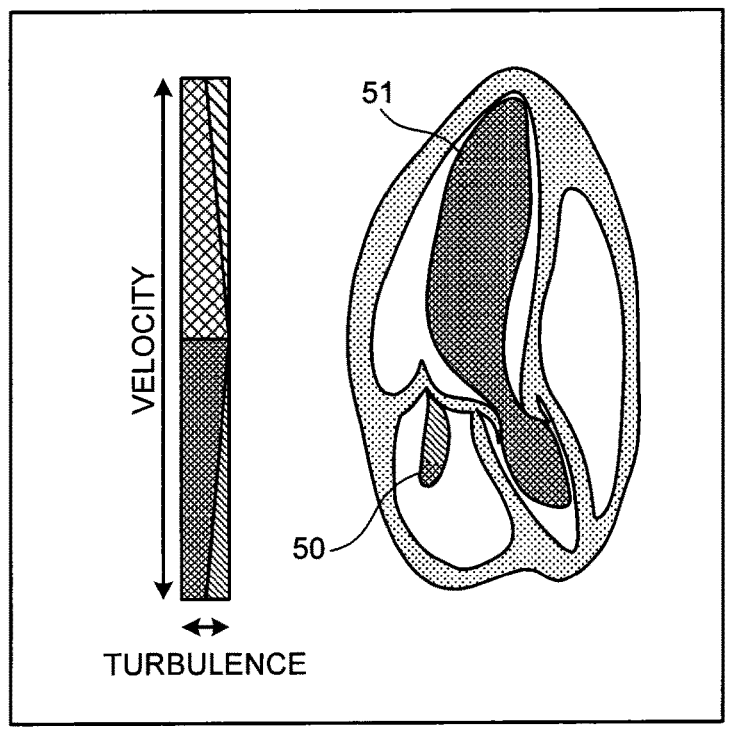
FIG. 5 is a schematic for explaining an example of an issue to be addressed in the first embodiment.

Explained now is an example in which the image visibility is degraded in an examination conducted with an ultrasonic diagnostic apparatus. FIG. 5 is a schematic for explaining an example of an issue to be addressed in the first embodiment. FIG. 5 depicts how an intracardiac blood flow is displayed in a CDI. In other words, the image of the intracardiac blood flow illustrated in FIG. 5 is an image on which a color Doppler image of a reverse blood flow 50 and a normal blood flow 51 is superimposed over a B-mode image of a heart. Illustrated in FIG. 5 is velocity (V)—turbulence (variance) (T) representation that allows the reverse blood flow 50 to be observed, taking advantage of the fact that the reverse blood flow 50 has a higher turbulence than that of the normal blood flow 51. In the V-T representation, for example, when there is a reverse blood flow, as illustrated in FIG. 5, the reverse blood flow 50 is displayed in a different color than that of the normal blood flow 51.

At this time, if a representation time for the reverse blood flow 50 illustrated in FIG. 5 is short, or the reverse blood flow 50 is temporally and spatially overlapped with the normal blood flow 51 or an artifact, for example, observations of the reverse blood flow 50 become difficult. In other words, the visibility of the image is degraded, and as a result, diagnostic accuracy or the throughput might be reduced.

Described now are some more examples of degraded image visibility other than that described above. For example, in an ultrasound contrast examination using a contrast agent, echo signals from the contrast agent are displayed in an emphasized manner, while echo signals from the tissues are suppressed. In such a case, image visibility could degrade because signals resulted from the tissues might be included in harmonics or subharmonics that are echo signals from the contrast agent. Furthermore, when a coronary blood flow is observed using a CDI, the image visibility could be degraded by clutter artifacts that are generated by the movement of myocardia (artifacts in which tissue Doppler signals are mixed).

Therefore, an object of the present application is to improve the image visibility in situations such as those explained above. The controller 170 for executing control for improving the image visibility will be now explained in detail.

Figure 6:
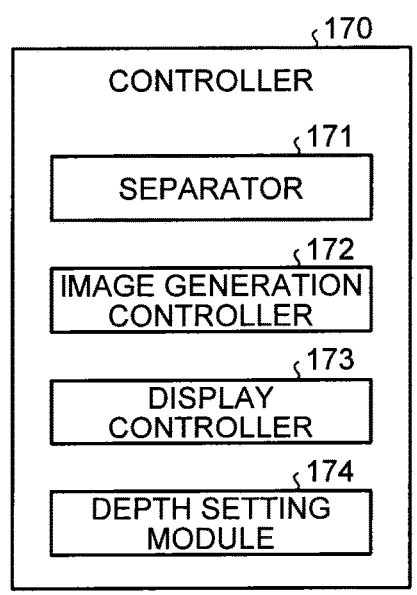
FIG. 6 is a schematic of an example of a configuration of a controller in the first embodiment.

FIG. 6 is a schematic of an example of a configuration of the controller 170 according to the first embodiment. As illustrated in FIG. 6, the controller 170 includes a separator 171, an image generation controller 172, a display controller 173, and a depth setting module 174.

The separator 171 separates an arbitrary region of a displayed object represented from image data, in a depth direction, based on a characterizing quantity included in the image data. Specifically, the separator 171 extracts a region represented from image data including a characterizing quantity within a range specified by a given threshold, as an arbitrary region of a displayed object. As the characterizing quantity, the separator 171 uses at least one of velocity information, turbulence information, and power information acquired through the color Doppler method. The image data represents velocity-related information, and the separator 171 separates a region by using turbulence as a characterizing quantity so that a region with a higher turbulence is arranged closer to the viewer. The separator 171 also uses luminance information as a characterizing quantity. Used in the first embodiment is an example in which turbulence information acquired by the color Doppler method is used.

Figure 7A:
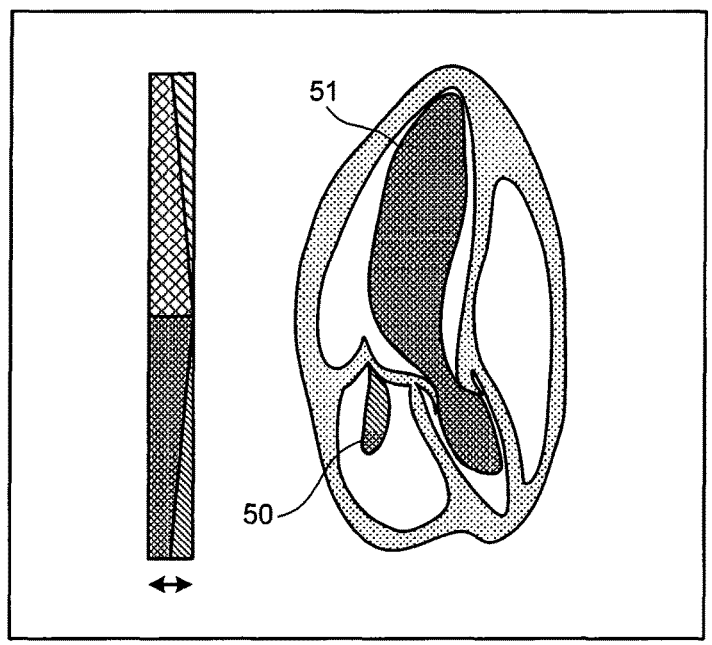
FIG. 7A is a schematic for explaining an example of a process performed by a separator in the first embodiment.
Figure 7B:
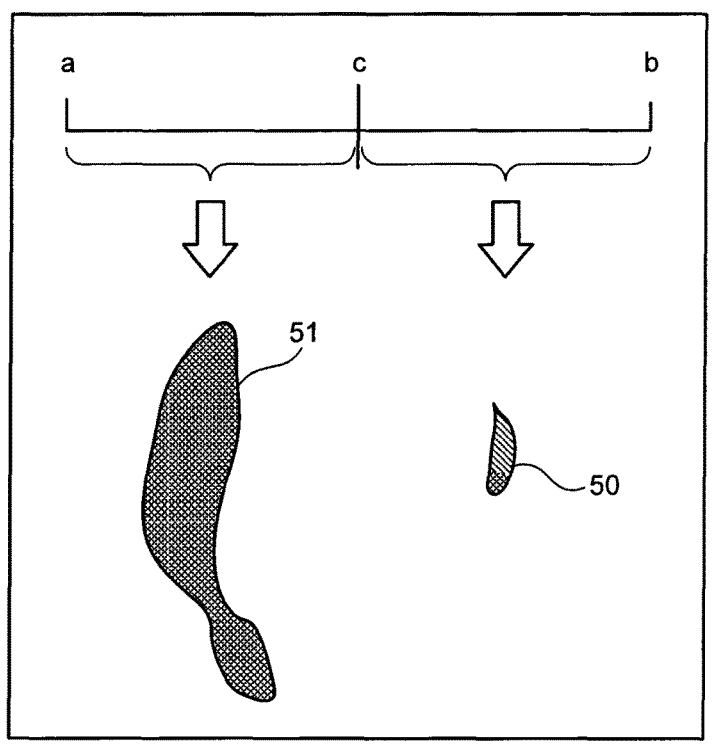
FIG. 7B is a schematic for explaining the example of the process performed by the separator in the first embodiment.

FIGS. 7A and 7B are schematics for explaining an example of a process performed by the separator 171 according to the first embodiment. FIGS. 7A and 7B illustrate an example in which the turbulence in the CDI data for the intracardiac blood flow illustrated in FIG. 5 is used. For example, the separator 171 separates a target region of the intracardiac blood flow in the depth direction using the turbulence indicated by the arrow in FIG. 7A.

To explain with an example, to begin with, the separator 171 separates turbulence ranging from "a to b" into two sections "a to c" and "c to b", using a threshold "c", as illustrated in FIG. 7B. The separator 171 then separates a group of pixels representing the intracardiac blood flow into two groups of pixels based on the turbulence. For example, the separator 171 separates a group of pixels representing the intracardiac blood flow into a region representing the normal blood flow 51, which has a turbulence within the range "a-c", and a region representing the reverse blood flow 50, which has a turbulence within the range "c-b", as illustrated in FIG. 7B. The threshold may be specified by the operator in advance, or each system may be provided with a unique threshold. The threshold may also be set automatically based on the turbulence acquired. Furthermore, the threshold may also be selected from a plurality of preset alternatives depending on a situation (e.g., depending on a displayed object, or a characterizing quantity being used). A region in the B-mode image for which no CDI data is collected (e.g., cardiac valve or cardiac wall) may be excluded from the separation, or separated by setting "zero" to the characterizing quantity (turbulence in the example explained above) of the region. Alternatively, the separator 171 may determine whether such a region is separated depending on a situation (e.g., depending on a displayed object, or a characterizing quantity being used).

Referring back to FIG. 6, the image generation controller 172 generates an image to be displayed in which depth direction information is reflected on an arbitrary region of the displayed object, separated by the separator 171. Specifically, the image generation controller 172 causes the image generator 140 to generate virtual volume data in which two-dimensional images representing regions separated by the separator 171 are arranged in the depth direction within a virtual space based on the turbulence. The image generation controller 172 then causes the image generator 140 to generate a parallax image group to be displayed by causing the image generator 140 to apply a volume rendering process to the virtual volume data thus generated while changing the viewpoint by the parallax number from a given direction.

FIG. 8 is a schematic for explaining an example of a process performed by the image generation controller 172 according to the first embodiment. For example, the image generation controller 172 places the two-dimensional images representing the reverse blood flow 50 and the two-dimensional image representing the normal blood flow 51, both of which are separated by the separator 171, in a depth direction set in advance based on the turbulence, as illustrated as (A) in FIG. 8. In other words, as illustrated as (A) in FIG. 8, the image generation controller 172 places the two-dimensional image representing the normal blood flow 51 in front of the two-dimensional image that is a B-mode image representing the heart, and places the two-dimensional image representing the reverse blood flow 50 in front of the two-dimensional image representing the normal blood flow 51. In other words, the image generation controller 172 places the two-dimensional images separated by the separator 171 in such a way that a region with a higher turbulence is arranged closer to the viewer, exactly in the manner separated by the separator 171 in a virtual space.

The image generation controller 172 causes the image generator 140 to generate virtual volume data in which the two-dimensional image representing the reverse blood flow 50, the two-dimensional image representing the normal blood flow 51, and the two-dimensional image representing the heart are arranged sequentially in the depth direction in the virtual space, as illustrated as (B) in FIG. 8. The image generation controller 172 then causes the image generator 140 to generate a parallax image group to be displayed by executing the volume rendering process from the direction of arrow 300, illustrated in FIG. 8, based on the parallax number, for example. An interval between the two-dimensional images in the depth direction, the line of sight used in executing the volume rendering process, the parallax angle, and the like may be specified to given values by the operator, or each system may be provided with unique settings. Alternatively, these values may be set automatically based on the turbulence acquired. Furthermore, the interval between the two-dimensional images in the depth direction, the line of sight used in executing the volume rendering process, the parallax angle, and the like may also be selected from a plurality of preset alternatives depending on a situation (e.g., depending on a displayed object, or a characterizing quantity being used).

Referring back to FIG. 6, the display controller 173 causes the monitor 13 to display the parallax image group generated under the control of the image generation controller 172. For example, the display controller 173 causes the monitor 13 to display the parallax image group generated by applying the volume rendering process to the virtual volume data illustrated in (B) in FIG. 8, with nine viewpoints from the direction indicated by the arrow 300.

As described above, in the ultrasonic diagnostic apparatus 1 according to the first embodiment, the image visibility is improved by presenting a stereoscopic image providing stereoscopic view of a region of interest to the operator.

Referring back to FIG. 6, the depth setting module 174 sets depth direction information included in the image to be displayed generated by the image generator, based on an operation of the operator. Specifically, when the operator makes an input operation via the input device 12 while observing the stereoscopic image displayed on the monitor 13, the depth setting module 174 changes the depth of the stereoscopic image based on the operation. In other words, the depth setting module 174 displays the stereoscopic image in a changed depth, by causing the image generator 140 to generate a parallax image group after increasing or reducing the depth-direction interval between the two-dimensional images arranged in the virtual volume data from which the stereoscopic image currently being displayed is generated, and by causing the monitor 13 to display the parallax image group.

FIG. 9 is a schematic for explaining an example process performed by the depth setting module 174 according to the first embodiment. FIG. 9 illustrates an example in which a corresponding relationship between the depth and the turbulence is in a proportional relationship. For example, the depth setting module 174 causes the monitor 13 to display a graph indicating the relationship between the depth and the turbulence, as illustrated in FIG. 9. The depth setting module 174 then changes the depth of the stereoscopic image based on an inclination of a line 301 changed by the operator via the input device 12.

To explain using an example, to emphasize the feel of depth, the operator changes the inclination of the line 301 illustrated in (A) in FIG. 9 to the inclination of the line 301 illustrated in (B) in FIG. 9. The depth setting module 174 then displays a stereoscopic image having a larger depth by increasing the depth-direction interval between the two-dimensional images arranged in the virtual volume data from which the stereoscopic image currently being displayed is generated, based on a change in the inclination, causing the image generator 140 to generate a parallax image group, and causing the monitor 13 to display the parallax image group. By contrast, to suppress the feel of depth, the operator changes the inclination of the line 301 illustrated in (B) in FIG. 9 to the inclination of the line 301 illustrated in (A) in FIG. 9, for example.

As described above, the ultrasonic diagnostic apparatus 1 according to the first embodiment can also receive a depth setting performed by the operator, whereby images further improved in visibility can be provided.

Explained in the first embodiment is an example in which the turbulence in the CDI is used; however, the displayed object can also be separated into target regions by using velocity or power in the CDI data generated by the Doppler processor 130, or luminance included in the B-mode data generated by the B-mode processor 120.

A process performed by the ultrasonic diagnostic apparatus 1 according to the first embodiment will now be explained with reference to FIG. 10. FIG. 10 is a flowchart illustrating the process performed by the ultrasonic diagnostic apparatus 1 according to the first embodiment. As illustrated in FIG. 10, in the ultrasonic diagnostic apparatus 1 according to the first embodiment, if a visibility improvement mode is ON (Yes at Step S101), the separator 171 acquires characterizing quantity information (for example, turbulence, velocity, power, luminance) (Step S102).

The separator 171 separates a displayed object based on the characterizing quantity thus acquired and a preset threshold (Step S103). The image generation controller 172 then sets a depth in which the two-dimensional images of the regions that are separated by the separator 171 are arranged (Step S104), and generates the virtual volume data (Step S105).

The image generation controller 172 then applies a rendering process to the virtual volume data thus generated, based on the parallax number (Step S106). The display controller 173 then causes the monitor 13 to display a parallax image group generated under the control of the image generation controller 172 (Step S107). The depth setting module 174 then determines if a depth change request for changing the depth has been received (Step S108).

If a depth change request has been received (Yes at Step S108), the depth setting module 174 returns to Step S104, and sets the depth of the image. By contrast, if a depth change request has not been received (No at Step S108), the ultrasonic diagnostic apparatus 1 according to the first embodiment ends the process.

As described above, according to the first embodiment, the separator 171 separates an arbitrary region of a displayed object represented from the image data, in a depth direction, based on a characterizing quantity included in the image data. The image generation controller 172 generates an image to be displayed in which depth direction information is reflected on the arbitrary region of the displayed object separated by the separator 171. The display controller 173 displays the image to be displayed generated by the image generation controller 172 onto the monitor 13 that is capable of providing a stereoscopic vision. Therefore, the ultrasonic diagnostic apparatus 1 according to the first embodiment can provide a stereoscopic vision of a region of interest, and the image visibility can be improved. Furthermore, by improving the image visibility, the ultrasonic diagnostic apparatus 1 according to the first embodiment can improve diagnostic accuracy and diagnostic throughput.

Furthermore, according to the first embodiment, the separator 171 uses at least one of velocity information, turbulence information, and power information acquired through the color Doppler method as the characterizing quantity. Therefore, when the reverse blood flow or the coronary blood flow is to be observed, the ultrasonic diagnostic apparatus 1 according to the first embodiment enables the visibility of each of these regions to be specifically improved.

Furthermore, according to the first embodiment, the image data represents velocity-related information, and the separator 171 uses turbulence as a characterizing quantity, and performs separation so that a region with a higher turbulence is arranged closer to the viewer. Therefore, the ultrasonic diagnostic apparatus 1 according to the first embodiment allows a region in which the observer is interested to be displayed closer to the viewer. Thus, the image visibility can be further improved.

Furthermore, according to the first embodiment, the separator 171 uses luminance information as a characterizing quantity. Therefore, the ultrasonic diagnostic apparatus 1 according to the first embodiment can improve the visibility of a region of interest specifically, in an examination using a contrast agent.

For example, in the contrast-echo method that allows a blood flow behavior to be observed clearly by injecting microbubbles and the like into a vein as a contrast agent and amplifying the blood flow signal, the ultrasonic diagnostic apparatus 1 according to the first embodiment can specifically improve the visibility of the blood flow behavior represented in the contrast image, and can improve diagnostic accuracy and diagnostic throughput, such as differential diagnosis of a cancer or diffuse liver disease diagnosis, such as chronic hepatitis and cirrhosis.

Furthermore, according to the first embodiment, the separator 171 extracts a region represented from image data including a characterizing quantity within a range specified by a given threshold as an arbitrary region of a displayed object. Therefore, the ultrasonic diagnostic apparatus 1 according to the first embodiment can display regions with close characterizing quantities in the same depth, to enable the image visibility to be improved further.

For example, if a highly granular depth is established in a space based on the characterizing quantity, regions located near to each other might be allocated to depths that are greatly different from each other. To explain using an example, turbulence might vary within the same reverse blood flow. Therefore, if such variation is reflected on the depth, the visibility is degraded. The ultrasonic diagnostic apparatus 1 according to the first embodiment enables degradation of visibility caused by variation in the characterizing quantity as explained above to be avoided.

Furthermore, according to the first embodiment, the depth setting module 174 changes the depth direction information included in the image to be displayed generated by the image generation controller 172, based on an operation of an operator. The image generation controller 172 then generates an image to be displayed on which the depth direction information set by the depth setting module 174 is reflected. The ultrasonic diagnostic apparatus 1 according to the first embodiment can also receive a depth setting from the operator, whereby an image with higher visibility can be provided.

Second Embodiment

While the first embodiment is described above, embodiments other than the first embodiment are still possible.

Explained in the first embodiment is an example in which a stereoscopic image is generated and displayed by the ultrasonic diagnostic apparatus 1. However, embodiments are not limited thereto, and may represent an example in which a stereoscopic image is generated and displayed by an image processing apparatus, for example. In such an implementation, for example, the image processing apparatus acquires B-mode image data and Doppler image data, separates regions of a displayed object based on characterizing quantities (velocity, turbulence, power, and luminance), and generates virtual volume data in which two-dimensional images representing the regions thus separated are positioned at different positions in a depth direction within a virtual space. The image processing apparatus then generates a parallax image group from the virtual volume data thus generated based on the parallax number, and displays the parallax image group.

Furthermore, explained in the first embodiment is an example in which two-dimensional B-mode image data and Doppler image data are used. However, embodiments are not limited thereto, and may represent an example in which three-dimensional B-mode image data and Doppler image data are used. In such an example, an MPR image or a volume rendering image generated from three-dimensional B-mode image data and Doppler image data are used as an initial image, and a stereoscopic image is generated based on the characterizing quantity in the initial image.

Furthermore, explained in the first embodiment is an example in which regions of a displayed object are separated using a single threshold. However, embodiments are not limited thereto, and may also represent an example in which two or more thresholds are used, for example.

Furthermore, explained in the first embodiment is an example in which a threshold separating the entire range of the characterizing quantity (turbulence) into two sections is used. However, embodiments are not limited thereto, and may represent an example using a threshold allowing a region having a characterizing quantity within a specific range in the entire range of the characterizing quantity to be separated, for example. For example, thresholds may be given to the turbulence "a-b" illustrated in FIG. 7B in such a way that "a<c1 to c2<d1 to d2<b", and regions indicating a characterizing quantity within the range "c1 to c2" and the range "d1 to d2" may be separated.

Furthermore, explained in the first embodiment is an example in which the threshold is preset. However, embodiments are not limited thereto, and may represent an example in which the threshold is set automatically using color Doppler image data. In such an example, for example, the turbulence included in the Doppler image data is expressed in a normal distribution, and a threshold for separating a specific region is specified.

Explained in the first embodiment is an example in which the depth of the stereoscopic image is changed by changing the interval at which the two-dimensional images are arranged in the virtual volume data. However, embodiments are not limited thereto, and may represent an example in which the depth of the stereoscopic image is changed by changing the parallax angle used in performing the volume rendering process, for example.

Explained in the first embodiment is an example in which a single characterizing quantity is used. However, embodiments are not limited thereto, and may represent an example in which two or more different characterizing quantities are used, for example.

As explained above, according to the first embodiment and the second embodiment, image visibility can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
a controller configured to
separate color Doppler image data into a plurality of groups, wherein each group represents a region in an imaged object,
wherein separating the image data into a plurality of groups comprises separating pixels included in the image data into the plurality of groups based on turbulence of each pixel included in the image data and a given threshold,
generate virtual volume data in which each of the plurality of groups comprises a two-dimensional image arranged in a depth direction in a virtual space with groups having a higher turbulence being arranged closer to a viewer, and
generate a stereoscopic image to be displayed in which each group in the virtual volume is displayed stereoscopically at a position corresponding to the turbulence in the depth direction within the stereoscopic image, by applying a volume rendering process to the virtual volume data; and
a display configured to display the stereoscopic image.

2. The ultrasonic diagnostic apparatus according to claim 1, wherein the controller is configured to separate the pixels based on at least one of velocity and power in addition to the turbulence.

3. The ultrasonic diagnostic apparatus according to claim 2, wherein the controller is configured to further separate the pixels based on luminance information.

4. The ultrasonic diagnostic apparatus according to claim 1, wherein the controller is configured to separate the pixels based on luminance information in addition to the turbulence.

5. The ultrasonic diagnostic apparatus according to claim 1, wherein the controller is configured to extract the groups comprising pixels with turbulence within a range specified by the given threshold.

6. The ultrasonic diagnostic apparatus according to claim 1, wherein the controller is further configured to change depth direction information associated with the stereoscopic image to be displayed, based on an operation of an operator, and generate an updated stereoscopic image to be displayed on which the depth direction information set is reflected.

7. The ultrasonic diagnostic apparatus according to claim 1, wherein the controller is further configured to separate the color Doppler image data by separating pixels representing intracardiac blood flow into a first group representing normal blood flow and a second group representing reverse blood flow, to generate second virtual volume data comprising a two-dimensional image of the first group and a two-dimensional image of the second group, wherein the two-dimensional image of the second group is arranged closer to the viewer in the depth direction than the two-dimensional image of the first group, and cause the display to display an image corresponding to the second virtual volume data.

8. The ultrasonic diagnostic apparatus according to claim 1, wherein the controller is configured to automatically set the given threshold using the color Doppler image data.

9. An image processing apparatus comprising:
a controller configured to
separate color Doppler image data into a plurality of groups, wherein each group represents a region in an imaged object,
wherein separating the image data into a plurality of groups comprises separating pixels included in the image data into the plurality of groups based on turbulence of each pixel included in the image data and a given threshold, generate virtual volume data in which each of the plurality of groups comprises a two-dimensional image arranged in a depth direction in a virtual space with groups having a higher turbulence being arranged closer to a viewer, generate a stereoscopic image to be displayed in which each group in the virtual volume is displayed stereoscopically at a position corresponding to the turbulence in the depth direction within the stereoscopic image, by applying a volume rendering process to the virtual volume data, and cause a display to display the stereoscopic image.

10. A method comprising:

separating, using a controller, color Doppler image data into a plurality of groups, wherein each group represents a region in an imaged object, wherein separating the image data into a plurality of groups comprises separating pixels included in the image data into the plurality of groups based on turbulence of each pixel included in the image data and a given threshold;

generating, using the controller, virtual volume data in which each of the plurality of groups comprises a two-dimensional image arranged in a depth direction in a virtual space with groups having a higher turbulence being arranged closer to a viewer;

generating, using the controller, a stereoscopic image to be displayed in which each group in the virtual volume is displayed stereoscopically at a position corresponding to the turbulence in the depth direction within the stereoscopic image, by applying a volume rendering process to the virtual volume data; and causing a display to display the stereoscopic image.

* * * * *